US011103169B2

(12) United States Patent
Pierce et al.

(10) Patent No.: US 11,103,169 B2
(45) Date of Patent: Aug. 31, 2021

(54) SYSTEMS AND METHODS FOR A BLOOD COLLECTOR WITH ENHANCED VOLUME USING CAPILLARY TECHNIQUES

(71) Applicant: POLYMER TECHNOLOGY SYSTEMS, INC., Indianapolis, IN (US)

(72) Inventors: Jeffrey A. Pierce, Redwood City, CA (US); Bao Phan, San Jose, CA (US)

(73) Assignee: Polymer Technology Systems, Inc., Whitestown, IN (US)

( * ) Notice: Subject to any disclaimer, the term of this patent is extended or adjusted under 35 U.S.C. 154(b) by 481 days.

(21) Appl. No.: 15/435,797

(22) Filed: Feb. 17, 2017

(65) Prior Publication Data
US 2017/0231540 A1 Aug. 17, 2017

Related U.S. Application Data

(60) Provisional application No. 62/427,696, filed on Nov. 29, 2016, provisional application No. 62/296,467, filed on Feb. 17, 2016.

(51) Int. Cl.
*A61B 5/15* (2006.01)
*A61B 5/151* (2006.01)

(52) U.S. Cl.
CPC .... *A61B 5/150022* (2013.01); *A61B 5/15142* (2013.01); *A61B 5/150259* (2013.01); *A61B 5/150343* (2013.01)

(58) Field of Classification Search
CPC ........ A61B 5/150022; A61B 5/150259; A61B 5/150343; A61B 5/15142; A61B 5/150755; A61B 5/150213
See application file for complete search history.

(56) References Cited

U.S. PATENT DOCUMENTS

| 5,912,134 A | 6/1999 | Shartle |
| 2005/0196872 A1 | 9/2005 | Nguyen et al. |
| 2007/0299365 A1* | 12/2007 | Calasso ............. A61B 5/14532 600/583 |
| 2009/0318833 A1 | 12/2009 | Lim |
| 2012/0172820 A1 | 7/2012 | Cannehan et al. |
| 2013/0216452 A1 | 8/2013 | Phan et al. |
| 2014/0073990 A1 | 3/2014 | Holmes et al. |

FOREIGN PATENT DOCUMENTS

| CN | 103957794 A | 7/2014 |
| CN | 104968269 | 10/2015 |
| WO | WO2009059613 A1 | 5/2009 |

OTHER PUBLICATIONS

International Search Report dated Apr. 28, 2017 issued in parallel PCT App. No. PCT/US2017/018313 (2 pages).
International Written Opinion dated Apr. 28, 2017 issued in parallel PCT App. No. PCT/US2017/018313 (6 pages).
Office Action dated Nov. 4, 2020 issued in related Chinese Patent App. No. 201780023951.2 (18 pages).

* cited by examiner

*Primary Examiner* — Patrick Fernandes
(74) *Attorney, Agent, or Firm* — Haynes and Boone, LLP

(57) ABSTRACT

A blood sampler device includes a sampler body forming a hollow internal chamber with upper and lower openings, the sampler body including a sealing device disposed adjacent to the upper opening. The blood sampler device further includes a blood collector adapted to be inserted into the sampler body, the blood collector including a plurality of capillary channels.

14 Claims, 10 Drawing Sheets

SECTION A-A
SCALE 4:1

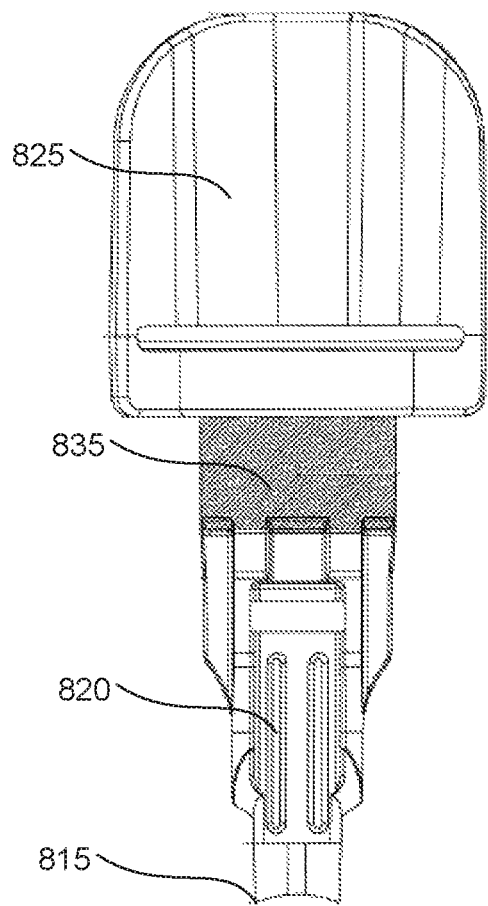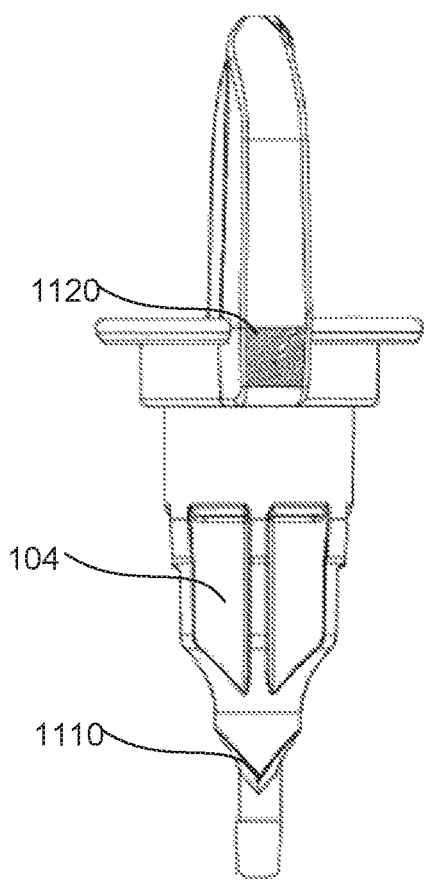

SYSTEMS AND METHODS FOR A BLOOD COLLECTOR WITH ENHANCED VOLUME USING CAPILLARY TECHNIQUES

CROSS REFERENCE TO RELATED APPLICATION

This application claims the benefit of U.S. Provisional Patent Applications No. 62/296,467 filed Feb. 17, 2016 and 62/427,696 filed Nov. 29, 2016, and hereby incorporated by reference to the same extent as though fully disclosed herein.

BACKGROUND

In many point-of-care systems for the testing of blood analytes, it is necessary to provide a blood collector and a mixing apparatus for the sample for a premix step. It is desirable to keep the size of such a system within certain limits while utilizing capillary channels in the blood collector. The size of a single capillary channel may have restrictions that may cause difficulty in developing such a configuration. Therefore, it may be desirable to create an alternative capillary system.

BRIEF SUMMARY

In one embodiment, a blood sampler device includes a sampler body forming a hollow internal chamber with upper and lower openings, the sampler body including a sealing device disposed adjacent to the upper opening. The blood sampler device further includes a blood collector adapted to be inserted into the sampler body, the blood collector including a plurality of capillary channels. In one alternative, the plurality of capillary channels include a first and second capillary channel. In another alternative, each of the first and second capillary channel include a pointed edge. Alternatively, the pointed edge is located distal from the center of the blood sampler device. Optionally, each of the plurality of capillary tubes includes a washout channel. In one alternative, the plurality of capillary channels is formed around a center of a bottom tip of the blood collector. In another alternative, the capillary channels are evenly spaced around the bottom tip. Optionally, the capillary channels are separated by a plurality of piercing structures. Alternatively, the plurality of piercing structures forms the bottom tip and is separated by breaks for the capillary channels. In one configuration, a support ring structure supports the plurality of piercing structures, and the plurality of piercing structures are open proximate to the bottom tip. In another configuration, the plurality of capillary channels continues from the bottom tip at an angle away from a longitudinal axis of the blood collector. Optionally, distal from the bottom tip, the blood collector includes a stop junction. Alternatively, each of the plurality of capillary tubes includes a washout channel. Optionally, the blood collector includes six capillary tubes, each capillary tube located radially 60 degrees from the adjacent two capillary tubes. In one alternative, the blood collector includes a seal surface extending around a circumference of the blood collector; a pair of ribs formed in a region adjacent to the seal surface; and at least one vent formed between the pair of ribs, the vent being adapted to allow air to escape from the chamber as the blood collector is inserted into the sampler body; and the vent comprising a top shoulder forming a gradually sloped surface adapted to smooth a flow profile of air flowing over the gradually sloped surface, wherein the seal surface engages the seal device to form a substantially airtight seal upon complete insertion of the blood collector into the sampler body. The vent is provided in response to the pressure that is generated when the blood collector is inserted into the sampler body. Without such a pressure release, the contents of the sampler/collector combination will be under pressure, which may result in undesired consequences, such as, during the release of the sample, an increased chance of spill may occur. Optionally, the gradually sloped surface comprises a substantially linear surface arranged at an angle with respect to the outer circumference of the seal surface. Alternatively, the pair of ribs each form an outer surface adapted to engage the sealing device as the blood collector is inserted into the sampler body.

In one embodiment, a blood collector includes a plurality of capillary channels for receiving a sample. In one alternative, the plurality of capillary channels include a first and second capillary channel. In another alternative, each of the first and second capillary channel include a pointed edge. Alternatively, the pointed edge is located distal from the center of the blood sampler device. Optionally, each of the plurality of capillary tubes includes a washout channel. Optionally, the plurality of capillary channels is formed around a center of a bottom tip of the blood collector. Alternatively, the capillary channels are evenly spaced around the bottom tip. In one alternative, the capillary channels are separated by a plurality of piercing structures. Optionally, the plurality of piercing structures forms the bottom tip and is separated by breaks for the capillary channels. Alternatively, a support ring structure supports the plurality of piercing structures, and the plurality of piercing structures are open proximate to the bottom tip. In one alternative, the plurality capillary channels continue from the bottom tip at an angle away from a longitudinal axis of the blood collector. In another alternative, distal from the bottom tip, the blood collector includes a stop junction. Optionally, each of the plurality of capillary tubes includes a washout channel. Alternatively, the blood collector includes six capillary tubes, each capillary tube located radially 60 degrees from the adjacent two capillary tubes.

BRIEF DESCRIPTION OF THE DRAWINGS

FIGS. 10A and 10B show two additional side views of the blood collector of FIG. 8;

DETAILED DESCRIPTION

Certain terminology is used herein for convenience only and is not to be taken as a limitation on the embodiments of the systems and methods for a blood collector with enhanced capillary collection. Shown in the figures generally are previous embodiments of a blood collector 99 and a new blood collector 100 which is configured to collect a greater sample. The new blood collector 100 has a substantially similar size and configuration so that it may fit with existing receivers. Additionally, blood collector 100a is provided. This is a different version of the collector 100 provided, incorporating many of the same principles as the collector 100. Collector 100a includes two capillary tubes instead of six. In the configuration of collector 100a, the two capillary tubes have been sized such that they can each intake approximately 20 microliters (20 μL) according to the capillary equation described below. This arrangement may also be advantageous, since the size of the washout slots may be increased, since the overall size of the capillary channel is increased.

An objective of the disclosed embodiments is to show an alternate blood collector design so that a larger blood sample could be used for various assays including, but not limited to, a cotinine assay currently produced and marketed by PTS Diagnostics. Some aspects of the design include the intent to continue to use all of the current elements of the A1CNow Sampler system, except that it is modified so the current blood collector portion of that system providing for a volume of blood collected from a finger prick (or blood drop from a vacutainer) would increase from 5 μL (required for A1CNow Test) to the 40 μL needed for the PTS Detect Cotinine assay and various other assays. Different assays may require different volumes of sample in order to run the different assays. Another objective of this disclosure is to provide designs and methods that provide for a variety of different sample sizes. By arranging capillary collectors as described in the various embodiments, one of ordinary skill in the art can create a variety of collectors with varying sample sizes, not just the 5 μL and the 40 μL described herein.

The current collection method relies on a capillary action, where a fluid is drawn up into a wetable capillary to a height, h, according to the following relation: where γ is the liquid-air surface tension (force/unit length), θ is the contact angle, ρ is the density of liquid (mass/volume), g is local acceleration due to gravity (length/square of time), and r is radius of tube (length). For the hypothetical situation where the capillary radius is identical to that specified for the current A1CNow Blood Collector, the fluid is water and the surface is glass that is completely wetted by water, one would expect the equilibrium height of the water in a vertical tube to be about 19.4 mm. This can be seen as a best-case rise height scenario.

Figures 1A, 1B:
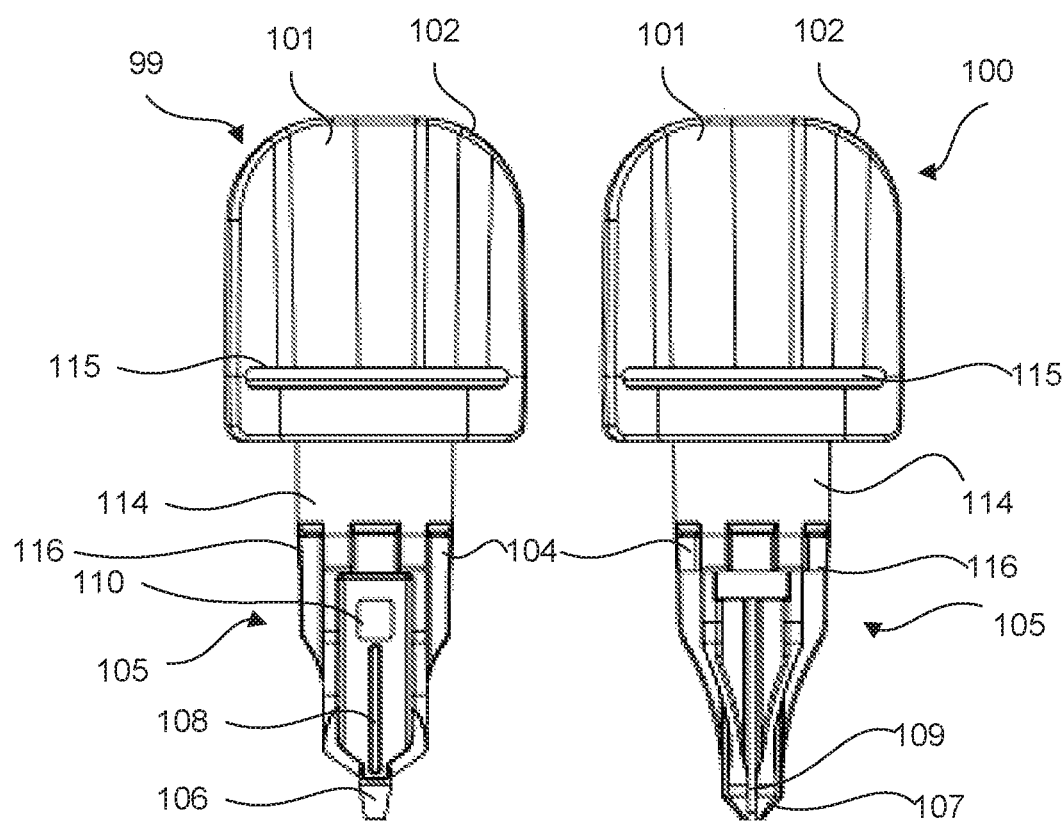
FIG. 1A shows one embodiment of a blood collector.
FIG. 1B shows one embodiment of a new blood collector with a plurality of capillary channels.

For the A1CNow assay, the capillary volume is 5 μL, the fluid is whole blood, the capillary material is a mildly hydrophilic polymer, and the capillary itself is slotted to allow the blood to wash out upon insertion into the sampler body (this is the embodiment shown in FIG. 1A). All of these changes lower the real-world possible rise height from the hypothetical case described above. It is for that reason that in some embodiments (like the six-capillary collector) our requirements so that the typical capillary fill angle is 45° rather than vertical. In this real-life situation, the blood collector fills completely (about 11 mm total length, 7.8 mm vertical height) in less than 6 seconds.

If one wanted to convert this system over to the blood collection needs for the PTS Detect Cotinine assay (40 μL) merely by increasing the blood collector capillary radius, trouble would ensue. To account for the eight-fold increase in volume, the capillary radius would need to increase by the square root of 8 (2.83 times). This would lower the capillary rise height by the same factor based on the above equation, so even in the best-case water/glass capillary example described above, the maximum possible rise height would be about 6.9 mm, which is below the needed vertical rise height of 7.8 mm when the capillary is filled at a 45° angle as described above. Adding in the rise height losses expected for the real system due to blood, a mildly hydrophilic plastic and a washout slot further doom this proposed solution. Lengthening the blood capillary would be another way to possibly collect more blood for the Cotinine assay, but we would need the capillary to be eight times longer, and the equation above tells us that we do not have that much additional rise height available to us. In reality, it will be difficult to increase the length much at all anyway, due to the design components of the remainder of the sampler system that we wish to retain.

The solution to the above problem is to convert the current A1CNow Blood Collector from a single capillary device to one that contains a multiplicity of capillaries, retaining the capillary filling potential of the capillary contained in the current blood collector, but multiplying the volume collected in the PTS Detect Cotinine blood collector through the multiplexing of the capillaries.

A size format for the proposed PTS Detect Cotinine blood collector is essentially equivalent to the A1CNow Blood Collector used in current practice. Although in many places herein the blood collector is suggested to be for a cotinine detection system, the blood collector may be used in various contexts and is not limited to cotinine. In some embodiments, the change in design is limited to the bottom 40% of the blood collector.

Figure 7:
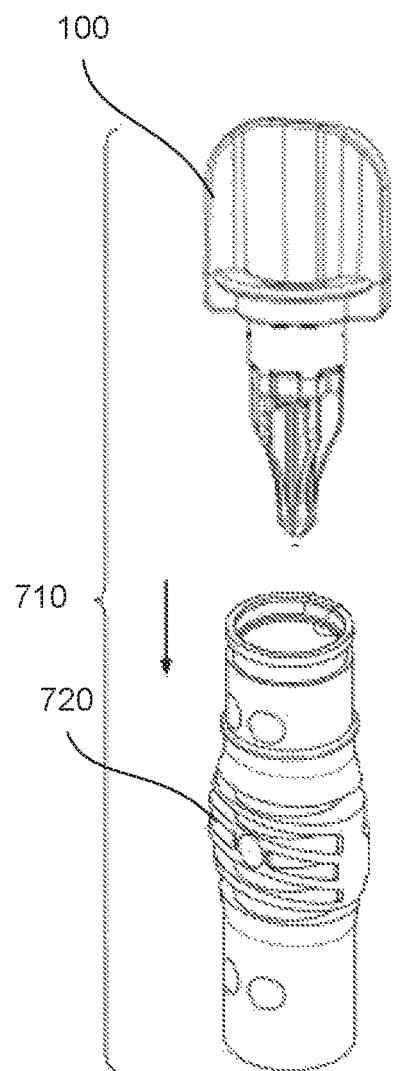
FIG. 7 shows a sample mixer including a receiver and the blood collector of FIG. 1B.

FIG. 1A shows one embodiment of a blood collector 99. Blood collector 99 collects a smaller amount of blood/sample (5 μL) and generally is used with the present A1C Now assay. As shown, blood collector 99 includes a tip 106, a capillary channel 108 and vents 104. Bottom tip 106 is formed on lower portion 105 of blood collector 99. In one example, bottom tip 106 is formed from a substantially hard material, such as a suitable polymer, plastic, metal, or other appropriate material, and in the shape of a cone, point, or other piercing element. In some embodiments, bottom tip 106 may be substantially sharp and/or may include a relatively small surface area in comparison with first septum, as will be discussed below. The sharp shape or small surface area enables bottom tip 106 to more easily penetrate the septum of a receiver such as shown in FIG. 7. An opening is formed adjacent the end of bottom tip 106 and provides an entrance into an internal capillary channel 108. Capillary channel 108 is formed as a substantially cylindrical tubular cavity, extending upwardly from an opening in bottom tip 106 to a stop junction 110. Stop junction 110 is an enlarged cavity portion of the capillary channel 108. In the exemplary embodiment shown, stop junction 110 has a substantially square cross-section. However, in other embodiments, stop junction 110 may include any other type of cross-section, such as substantially circular, rectangular, or another shape.

Blood collector 99 may include one or more flanges 115 adjacent to a lower end of handle 102. Flange 115 circumferentially extends around handle 102, providing one or more surfaces on which a user may exert pressure while inserting blood collector 99 into sampler body 720 (shown in FIG. 7) with reduced discomfort to the user. In some embodiments, flanges 115 may be widened in comparison with known devices. Below flange 115 is seal section 114 that seals with a sampler body to prevent a sample from escaping. Although not required, flanges 115 may include one or more indicators, such as arrows or another similar marking, to instruct a user to twist blood collector 99 in a particular direction while inserting blood collector 99 into sampler body 720. Handle 102 of blood collector 99 may be asymmetrically contoured to provide a user with a better grip of blood collector 99 when blood collector 99 is in use and inserted into sampler body 720. The handle 102 configuration allows a user to easily twist the blood collector 99 when placed into sampler body 720. The ability to twist blood collector 99 during the insertion of blood collector 99 can aid in reducing the insertion force required to insert blood collector 99 into sampler body 720.

Blood collector 100 as shown is a new blood collector 100 (also known as the six-capillary collector) with multiple capillary channels to accommodate an enhanced sample size. Blood collector 100 is designed to be used with the cotinine assay; however, it may be used for various analytes. Blood collector 100 generally is designed to collect 40 µL of sample. Many of the same features exist in the new blood collector 100 as the prior blood collector 99. The primary differences are that the bottom tip 106 has been replaced with tip 107. Tip 107 is segmented into six sections as is later apparent in the figures. This segmentation is to provide for the six capillary channels 109. By using six capillary channels 109, a much larger sample can be provided. As previously identified in relation to tip 106, tip 107 is rigid and somewhat sharp, such that it may pierce the septum of the receiver 720 (the septum is not shown). The collector also includes vents 104, as is similar to blood collector 99.

Six openings are formed adjacent the end of bottom tip 107 and provide an entrance into internal capillary channels 109. Capillary channels 109 (there are six of them) are formed as a substantially cylindrical tubular cavity, extending upwardly from the opening in bottom tip 107 to a stop junction, which will be discussed later. The stop junction is an enlarged cavity portion of each capillary channel 109. In embodiments, the stop junction may include any other type of cross-section, such as substantially circular, rectangular, or another shape.

Blood collector 100 may include one or more flanges 115 adjacent to a lower end of handle 102. Flange 115 circumferentially extends around handle 102, providing one or more surfaces on which a user may exert pressure while inserting blood collector 100 into sampler body 720 (shown in FIG. 7) with reduced discomfort to the user. In some embodiments, flanges 115 may be widened in comparison with known devices. Although not required, flanges 115 may include one or more indicators, such as arrows or another similar marking, to instruct a user to twist blood collector 100 in a particular direction while inserting blood collector 99 into sampler body 720. Handle 102 of blood collector 100 may be asymmetrically contoured to provide a user with a better grip of blood collector 100 when blood collector 99 is in use and inserted into the sampler body 720. The handle 102 configuration allows a user to easily twist the blood collector 100 when placed into sampler body 720. The ability to twist blood collector 100 during the insertion of blood collector 100 can aid in reducing the insertion force required to insert blood collector 100 into sampler body 720.

Referring to FIG. 7, there is shown a blood collector 100 disposed above a sampler body 720 of a blood sampler device 710 according to one embodiment. Referring to FIG. 1B, blood collector 100 includes a handle 102 at an upper portion 101 thereof to be gripped by a user. A lower portion 105 of blood collector 100 is dimensioned to be inserted forcibly by the user into sampler body 720, which generally is shaped as a hollow cylinder. A liquid chamber (not shown) is formed within sampler body 720, and contains a treatment solution, as well as air. The air in the liquid chamber becomes pressurized as blood collector 100 is inserted and, therefore, naturally seeks an area of lower pressure. Blood collector 100 includes a set of vents 104 that each allow air to escape as the liquid chamber becomes pressurized during the insertion of lower portion 105 of blood collector 100 into the liquid chamber, and thereby to control the resulting pressurization in the liquid chamber. In the exemplary embodiment shown, blood collector 100 includes six vents 104; however, other embodiments may include a different number of vents 104.

Sampler body 720 includes a first septum and a second septum that respectively form seals over a top and bottom of the liquid chamber. The tip 107 of blood collector 100 is designed to pierce the septum.

Figure 2:
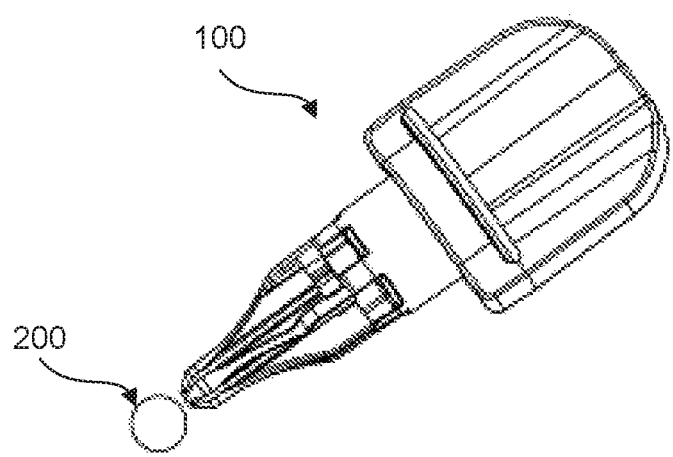
FIG. 2 shows one embodiment of a blood collector including a sample.

FIG. 2 shows one embodiment of a blood collector 100 including a circle 200, which denotes an approximate size of 40 µL blood drop when modeled as a hemispherical cap. A multiplicity of molded capillaries is contained in the PTS Detect Cotinine blood collector, all capable of feeding off of the same blood drop in parallel. In this embodiment of the design, there are six rectangular capillaries that are spaced 60 degrees apart radially and each runs axially up the blood collector with a volume sized to collect ⅙th of the needed blood (6⅔ µL per capillary) for a 40 µL fill volume. Capillaries contained within the PTS Detect Cotinine blood collector (blood collector 100) are sized such that the cross-section and length of each are more or less hydraulically equivalent to the single capillary that has worked effectively for the A1CNow blood collector.

Washout slots on each capillary of the PTS Detect Cotinine blood collector and a stop junction above each capillary so that blood can readily exit the capillaries through bulk movement and mix with a sample treatment buffer as the blood collector is inserted into the sampler body and the assembly is subsequently shaken by the user.

Figure 3A:
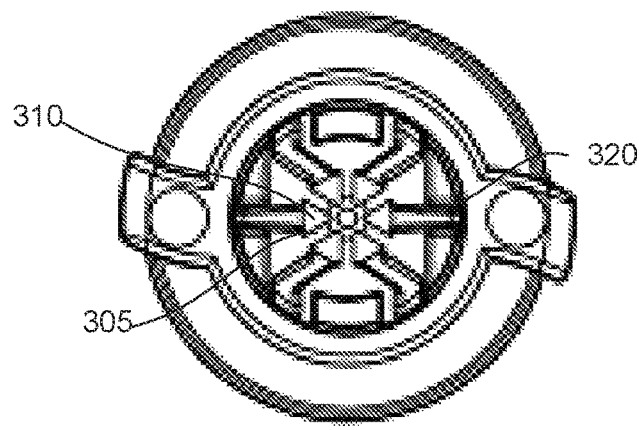
FIGS. 3A and 3B show detailed views of the tip of the blood collector of FIG. 1B.
Figure 3B:
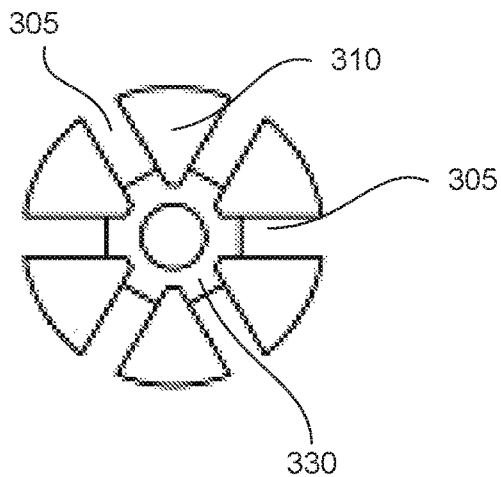

FIG. 3A shows a detailed view of one embodiment of the tip of the blood collector 100 from the bottom. As is visible, the tip 107 of the blood collector has six divided penetrating tips 310. This can further be seen in detail in the detailed view of FIG. 3B. The triangular penetrating tips 310 separate the capillary tube entrances 305. A support ring 330 provides support to the penetrating tips 310, such that they do not flex greatly when pressure is applied. Additionally, in FIG. 3A, the continuing form 320 of the penetrating tips 310 is visible. These forms 320 provide for a gradual tapering of the end of the blood collector 100.

Figure 4A:
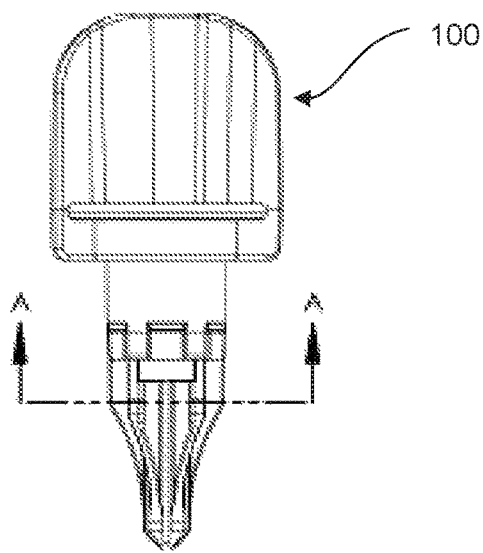
FIGS. 4A and 4B provide another view of the blood collector of FIG. 1B.
Figure 4B:
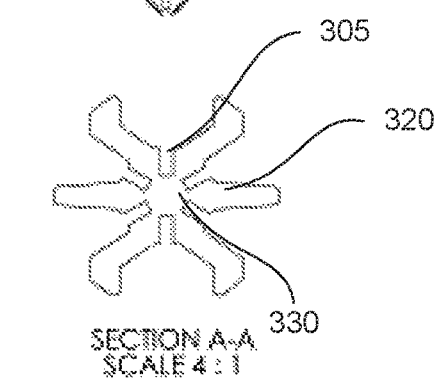

FIGS. 4A and 4B provide another view of blood collector 100. FIG. 4B is a cross-section of the blood collector taken through cut A. Visible in FIG. 4B are the supporting ring 330, the capillaries 305, and the forms 320.

Figure 5A:
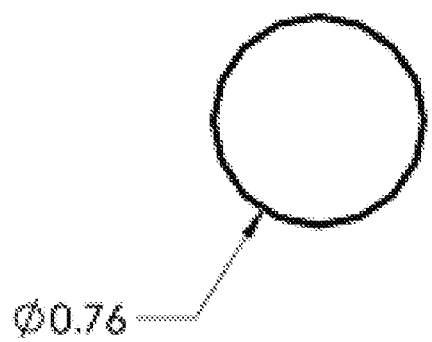
FIG. 5A shows a cross-section of the capillary tube of the blood sampler of FIG. 1A.
Figure 5B:
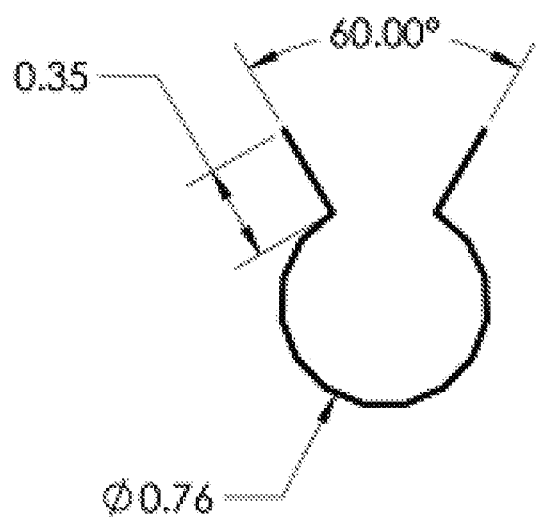
FIG. 5B shows a cross-section of a capillary tube of the blood sampler of FIG. 1A showing the capillary tube and washout slot geometry.
Figure 5C:
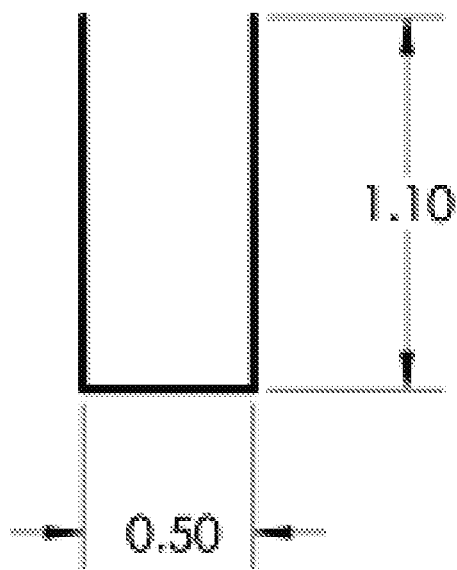
FIG. 5C shows a cross-section of the height of the capillary tube of the blood sampler of FIG. 1B.

FIG. 5A shows a cross-section of the capillary tube 108 of blood sampler 99. This previous system provides for an approximately circular capillary. FIG. 5B shows a cross-section of a capillary tube 108 of blood sampler 99 showing the washout slot. As is visible, the sampler has an open portion, also known as a washout slot, that allows for the escape of the sample when introduced into the sampler body 720. FIG. 5C shows the height cross-section of the capillary tube 109. All dimensions shown are in centimeters.

Figure 6A:
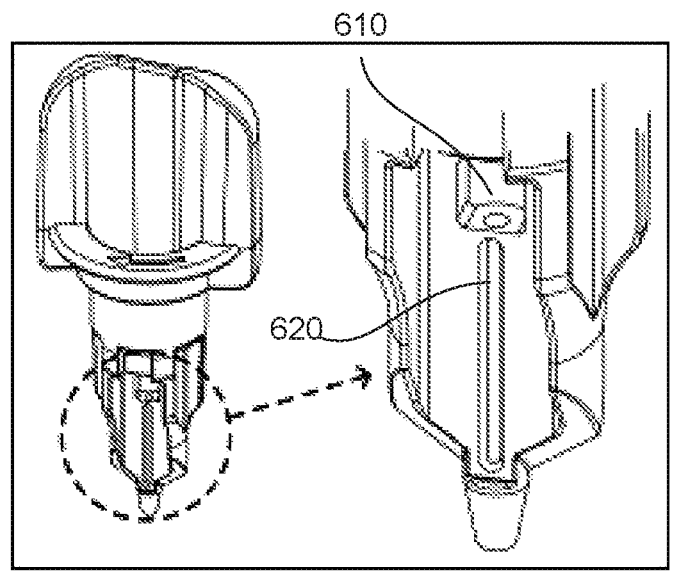
FIGS. 6A and 6B show the washout slot and the stop junction for the blood collector of both FIGS. 1A and 1B.
Figure 6B:
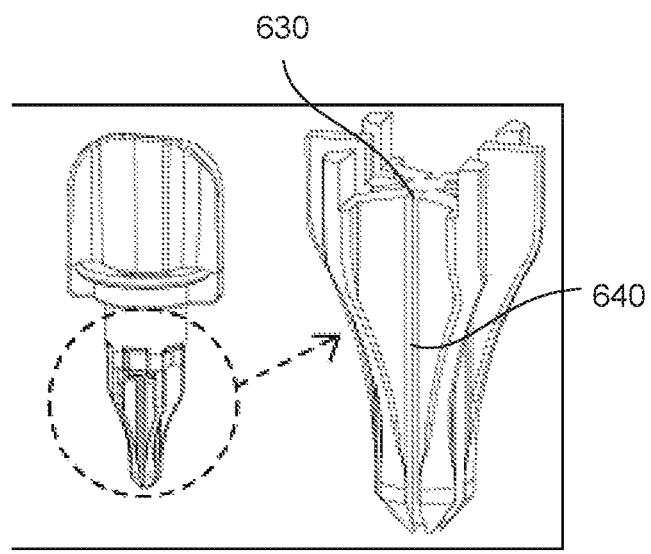

FIGS. 6A and 6B show the washout slot and the stop junction for both blood collector 99 and blood collector 100. FIG. 6A shows a detail view of blood collector 99. Blood collector 99 includes washout slot 620 and stop junction 610. In FIG. 6B, a detailed view of blood collector 100 is visible, showing washout slot 630 and stop junction 640.

FIG. 7 shows sample mixer 710 including receiver 720 and blood collector 100.

Figure 8:
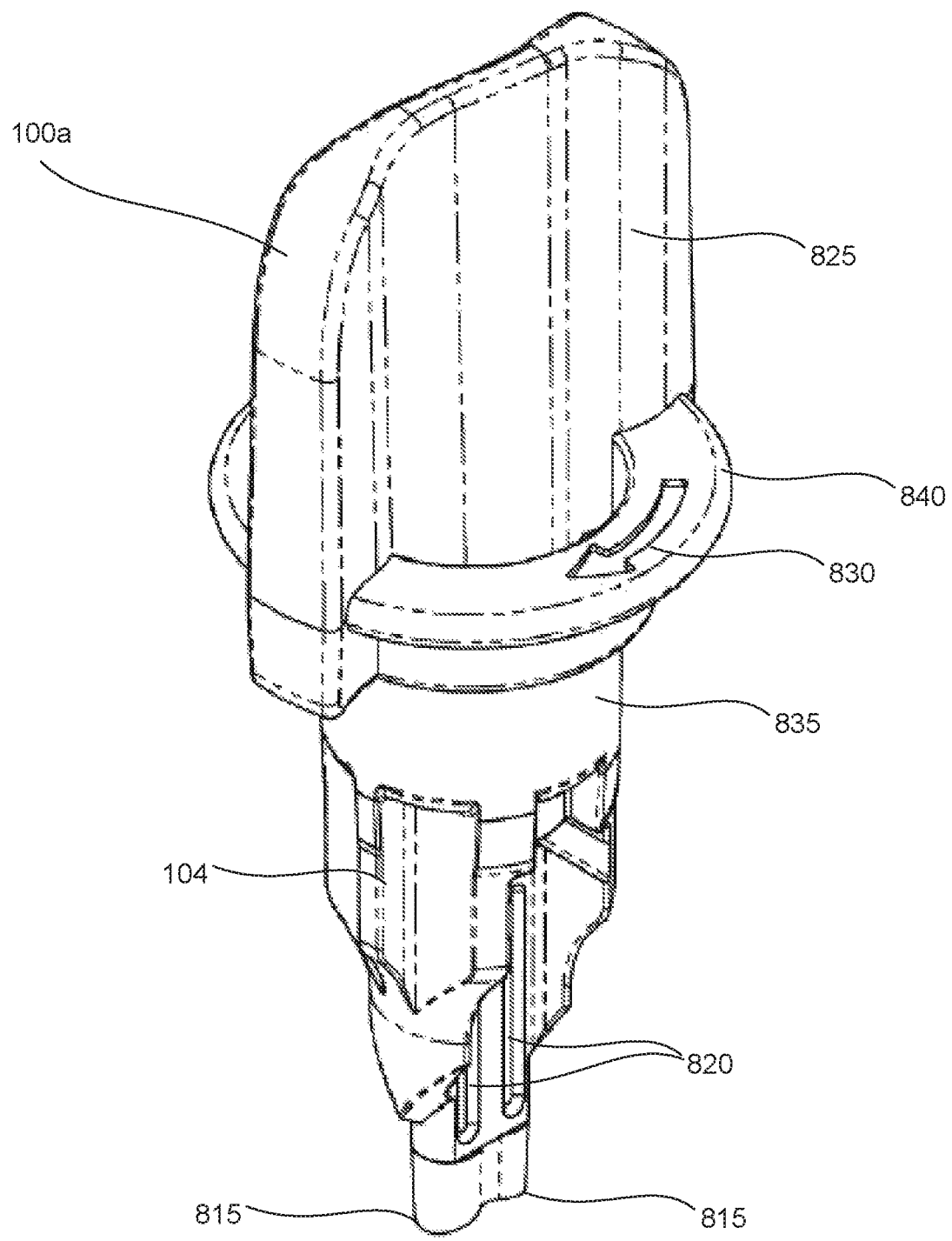
FIG. 8 shows a perspective view of an alternative embodiment of a blood collector having two capillary tubes.

FIG. 8 shows a perspective view of an alternative embodiment of a blood collector (100a) having two capillary tubes. Similar to the previous embodiment, the point of this collector is to increase the sample size to 40 microliters (40 µL). This enables the use of the collector/sampler system for a multitude of different assays that require a greater sample size. As explained above, the collector 100a is similarly insertable into a sampler body 720 in the same manner shown in FIG. 7 for collector 100. This enables a premix step and in many cases a two part mixing step, where the collector 100a penetrates a first liquid chamber and then is advanced to a second liquid chamber after a period of time. Therefore, as with previous embodiments, the collector 100a includes a pointed tip for penetrating the seals of the liquid chambers and vents for relieving the pressure and preventing the backflow of fluid as the collector 100a is inserted into a sampler body 720.

As shown in FIG. 8, collector 100a includes a first and second pointed capillary tip 815. These tips 815 are at the entrance to a first and second capillary tube. Each capillary tube extracts approximately 20 microliters of sample when contacted with a sample. A balance is maintained according to the expected sample viscosity and surface tension, the size of the sample needed, the number of capillary tubes that can contact the sample at once, and the required sample size. Capillary tip 815 is needed to pierce the septum/seal of the liquid chambers. These tips 815 are formed by angling the end of the capillary tube such they have a pointed tip. In the configuration shown, the pointed tips are distal from each other and distal from the center point of the collector 100a. Collector 100a includes vents 104, which function similarly to the embodiments described above. Visible are washout slots 820. These washout slots 820 enable the fluid in the capillary tubes to be readily mixed when the sampler 100a is inserted into the sampler body. Seal portion 835 provides for a sealing section to interface with the sampler. Flange 830 circumferentially extends around handle 825, providing one or more surfaces on which a user may exert pressure while inserting blood collector 100a into a sampler body (similarly to as shown in FIG. 7). Guide arrow 830 provides an indicator for the turning direction of the collector 100a to aid in the insertion and mixing when inserted into the sampler.

Figure 9:
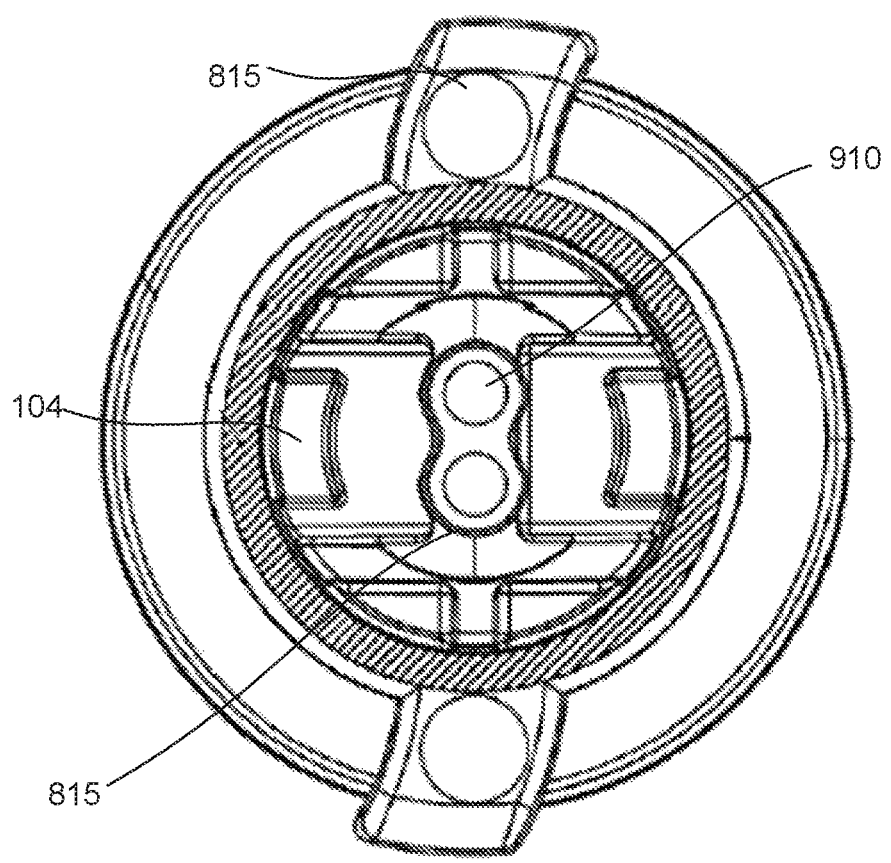
FIG. 9 shows a bottom view of the blood collector of FIG. 8.

FIG. 9 shows a bottom view of the blood collector of FIG. 8. Capillary tube openings 910 are shown as well as the location of capillary tips 815. A receiver 815 ejector pins is also shown in this view.

FIGS. 10A and 10B show two additional side views of the blood collector of FIG. 8. In this view, seal portion 835 is shaded, clearly showing the sealing portion of the collector 110a. Narrowed portion 1110 is additionally sharpened and narrowed to enable easier penetration of a septum or other seal. Area 1120 is the approximate location of a gate, upon insertion into a sampler.

Figure 11A:
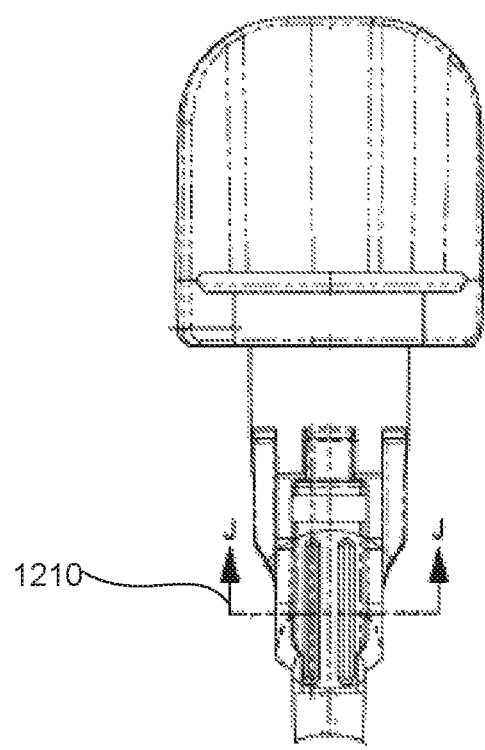
FIG. 11A shows a side view of the blood collector of FIG. 8 showing a cross-section line J-J.
Figure 11B:
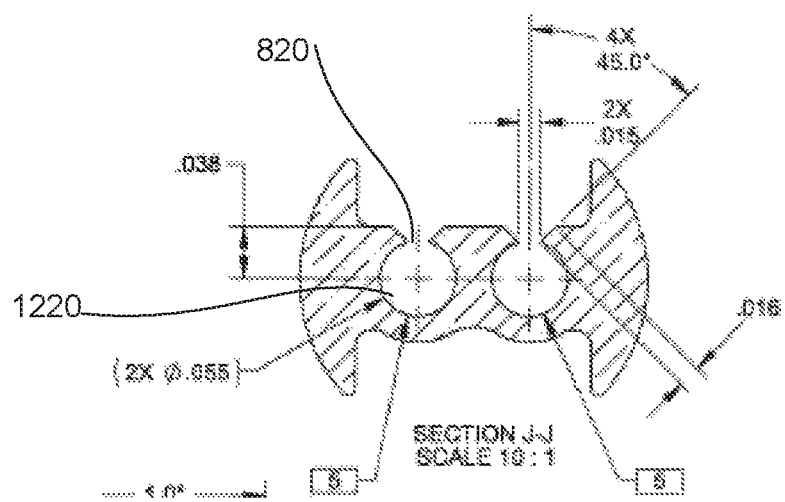
FIG. 11B shows the cross-section J-J.

FIG. 11A shows a side view of the blood collector of FIG. 8 showing a cross-section line J-J. FIG. 11B shows the cross-section J-J. Here the cross sectional area of the capillary tube 1220 is shown as well as the approximate configuration of the washout slots 820. As shown, the opening of the washout slots 820 are at approximately a 45 degree angle to the exterior of the collector 100a. In the configuration shown, both washout slots 820 are on the same side of the collector 100a, however in alternatives, the washout slots 820 may be on opposite sides.

The dual capillary collector, collector 100a has been tested with a cotinine assay to determine the reliability of the collector. The testing of this collector was tested against a pipette, the pipette representing what is believed to be a reliable sampler. A brief summary of the results from the preliminary testing is below:

| Part B: Cotinine Results with n = 10 testing spiked sample | Light Smoker: 40 µL Blood Collector (ng/mL) | Light Smoker: 40 µL DK Pipette (ng/mL) |
|---|---|---|
| Average | 127.4 | 127.1 |
| SD | 6.96 | 11.18 |
| % CV | 5.5% | 8.8% |
| Part A: Volume of whole blood collected with n = 10 (converted from mass) | New Blood Collector 40 µL (µL) | DK Pipette 40 µL (µL) |
| Average | 45.75 | 44.71 |
| SD | 0.71 | 0.89 |
| % CV | 1.6% | 2.0% |

Part B: Comparing the end/user results in terms of cotinine between the two sampling methods is definitely equivalent with an impressive (average) difference of less than 0.5 ng/mL.

Part A: Although both collectors appear to be collecting more sample than they should, this is likely due to the conversion from grams to µL based on the density of the whole blood sample used. Either way, it is easier to interpret the results in terms of µL. A difference of less than 1 µL is typically acceptable, such that it will not significantly affect the accuracy of a point of care test. Similarly, the precision is at least as good, if not better, than the DK pipettes that are currently employed in the cotinine assay.

Note, that typically, the collector and sampler combination are used in conjunction with a lateral flow test strip, such as in the case of the cotinine assay provided by Polymer Technology Systems, Inc. Such a test involves, obtaining a sample, typically by pricking a finger of an individual to be tested. Then the collector, such as the dual capillary collector 100a or the six-capillary collector 100, uses capillary action in order to intake the sample. The collector is then inserted into a sampler. In many cases the sampler includes a buffer. This buffer may be the only mixer in the sampler, or the sampler may include an additional mixer, contained in a separate compartment. Such compartment may contain antigens or antibodies, or some other reagent, with or without markers attached as the particular assay utilizes. In such a scenario a first septum, may separate a first compartment from the outside. The collector may penetrate the first septum. The buffer may then mix with the sample. The seal portion of the collector interfaces with the sampler and the vents allow for easy insertion by venting the air. The washout slots provide for easy mixing with the buffer. Subsequent to the initial mixing, the collector may be pushed through a second septum, sealing a second compartment containing an additional reactant or reactants. Subsequently, the sampler may be placed on a lateral flow test strip and a bottom septum may be broken in a variety of fashions, such that the sample is dosed on the lateral flow test strip. The sample may then react and flow across the lateral flow test strip and provide indicators to be visually read or read by a meter.

Note that in alternative embodiments, a different number or size of capillary tubes may be utilized. Generally, it is believed that there is a limit to the number of capillary tubes based on the pool of sample that will be contacted. Practically, there may be some normal situational constrains on the number however. Typically, the pool is a small droplet of blood obtained from a finger prick, so it is thought that 2-15 capillary tubes is likely the range of number of capillary tubes that can be used in alternative configurations. Note that more than 15 tubes may be used, especially if the size of the tube is significantly limited and the size of the sample pool is increased. Many embodiments of the collector also include additional similarities. Typically, the collectors include a sharpened tip or tips. In one configuration, the capillary tubes surround the sharpened tip, such as in the shown example of the six-capillary collector. In other configurations, the edges of the capillary tubes may be inclined relative to the inner edge (or visa-versa) and brought to a tip. In many scenarios, the single pointed tip or capillary tubes that are inclined and pointed in the center are typically most effective with configurations of more than three capillary tubes. Another common feature of the collectors is the inclusion washout slots, for mixing of the sample upon insertion into the sampler.

While specific embodiments have been described in detail in the foregoing detailed description, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A blood sampler device, comprising:
    a sampler body forming a hollow internal chamber with an upper opening and a lower opening, the sampler body including a sealing device disposed adjacent to the upper opening; and
    a blood collector adapted to be inserted into the sampler body, the blood collector including a plurality of capillary channels;
    wherein the plurality of capillary channels include a first capillary channel and a second capillary channel, each of the first capillary channel and the second capillary channel include a pointed edge at a bottom tip of the blood collector, the pointed edge a penetrating tip for penetrating a septum of a receiver, and the pointed edge of the first capillary channel is located distal from a center of the blood sampler device.

2. The blood sampler device of claim 1, wherein each of the plurality of capillary tubes includes a washout channel.

3. The blood sampler device of claim 1, wherein the plurality of capillary channels continues from the bottom tip at an angle away from a longitudinal axis of the blood collector.

4. The blood sampler device of claim 3, wherein distal from the bottom tip, the blood collector includes a stop junction.

5. The blood sampler device of claim 4, wherein each of the plurality of capillary channels includes a washout channel.

6. The blood sampler device of claim 5, wherein the blood collector includes six capillary tubes, each capillary tube of the six capillary tubes located radially 60 degrees from an adjacent two capillary tubes.

7. The blood sampler device of claim 6, wherein the blood collector includes:
    a seal surface extending around a circumference of the blood collector;
    a pair of ribs formed in a region adjacent to the seal surface; and
    at least one vent formed between the pair of ribs, the vent being adapted to allow air to escape from a chamber as the blood collector is inserted into the sampler body, and the vent comprising a top shoulder forming a gradually sloped surface adapted to smooth a flow profile of air flowing over the gradually sloped surface, wherein the seal surface engages a seal device to form a substantially airtight seal upon complete insertion of the blood collector into the sampler body.

8. The blood sampler device according to claim 7, wherein the gradually sloped surface comprises a substantially linear surface arranged at an angle with respect to the outer circumference of the seal surface.

9. The blood sampler device according to claim 8, wherein the pair of ribs each form an outer surface adapted to engage the sealing device as the blood collector is inserted into the sampler body.

10. A blood collector, comprising:
    a plurality of capillary channels for receiving a sample; wherein the plurality of capillary channels include a first capillary channel and a second capillary channel, each of the first capillary channel and the second capillary channel include a pointed edge at a bottom tip of the blood collector, the pointed edge a penetrating tip for penetrating a septum of a receiver, and the pointed edge of the first capillary channel is located distal from a center of the blood collector.

11. The blood collector of claim 10, wherein each of the plurality of capillary channels includes a washout channel.

12. The blood collector of claim 10, wherein the pointed edge of the first capillary channel is formed by angling an end of the first capillary channel and the pointed edge of the first capillary channel is on an outermost portion of the first capillary channel.

13. The blood collector of claim 12, wherein the pointed edge extends from an end of the blood collector to form a piercer for piercing a seal.

14. A blood sampler device, comprising:
    a sampler body forming a hollow internal chamber with an upper opening and a lower opening, the sampler body including a sealing device disposed adjacent to the upper opening; and
    a blood collector adapted to be inserted into the sampler body, the blood collector including a plurality of capillary channels; wherein the plurality of capillary channels are formed around a center of a bottom tip of the blood collector, the plurality of capillary channels are evenly spaced around the bottom tip, the plurality of capillary channels are separated by a plurality of piercing structures, the plurality of piercing structures forms the bottom tip and the bottom tip is separated by breaks into a plurality of sections, wherein the plurality of piercing structures are a penetrating tip for penetrating a septum of a receiver, the breaks being openings for the plurality of capillary channels, a support ring structure supports the plurality of piercing structures, and the plurality of piercing structures is open proximate to the bottom tip.

* * * * *